United States Patent [19]

Katayama et al.

[11] Patent Number: 4,816,194
[45] Date of Patent: Mar. 28, 1989

[54] METHOD OF DESTROYING A BRITTLE BODY BY HYDRATION EXPANSION

[75] Inventors: Takaaki Katayama, 3-9-10, Sakuragi, Kumamoto-shi, Kumamoto-ken; Shiro Ishii, Zushi; Koretoshi Hitotsuya, Ichikawa; Hachiro Kubota, Tokyo, all of Japan

[73] Assignees: Onoda Cement Co., Ltd; Takaaki Katayama, both of Japan

[21] Appl. No.: 810,989

[22] Filed: Dec. 19, 1985

[30] Foreign Application Priority Data

Dec. 21, 1984 [JP] Japan ................ 59-268580
Jul. 16, 1985 [JP] Japan ................ 60-155076
Jul. 16, 1985 [JP] Japan ................ 60-155077

[51] Int. Cl.⁴ ............... A61C 13/20; B29C 33/44
[52] U.S. Cl. ............... 264/16; 264/138; 264/221; 264/317; 264/DIG. 44; 433/213
[58] Field of Search ....... 264/221, 222, 317, DIG. 44, 264/DIG. 30, 313, 16, 17, 18, 19, 2.2, 2.4, 2.5, 28, 45.2, 67, 84, 118, 138, 140, 154, 155, 156, 219, 139, 294, 314, 319, 320, 334, 340, 343, 344, 349, DIG.39, 271.1; 425/DIG. 11, DIG. 12, 176, 436 RM, DIG. 14, DIG. 15, 27, 466, 467, DIG. 112; 249/54, 61, 62, 63, 64, 65, 142, 152, 178, 180, 160; 164/34, 37, 38, 69.1, 70.1, 131, 132, 320, 345; 72/58, 61, 150, 152, 370, 465, 466, 467; 433/45, 213

[56] References Cited

U.S. PATENT DOCUMENTS

| | | | |
|---|---|---|---|
| 2,217,734 | 10/1940 | Dreyfus | 264/317 |
| 2,739,350 | 3/1956 | Lampman | 264/313 |
| 3,213,163 | 10/1965 | Brite | 264/317 |
| 3,217,067 | 11/1965 | Tencate | 264/313 |
| 4,017,570 | 4/1977 | Rice | 264/84 |
| 4,252,760 | 2/1981 | Foster | 264/317 |
| 4,264,661 | 4/1981 | Brandolf | 264/317 |

FOREIGN PATENT DOCUMENTS

| | | | |
|---|---|---|---|
| 2188037 | 11/1958 | Australia | 264/317 |
| 0011130 | 1/1983 | Japan | 264/317 |
| 0018239 | 2/1983 | Japan | 264/317 |
| 0897551 | 1/1982 | U.S.S.R. | 264/317 |
| 563192 | 3/1944 | United Kingdom | 264/317 |
| 907629 | 6/1962 | United Kingdom | 264/84 |

OTHER PUBLICATIONS

American Machinists; G-15-59 "Exposive Forming".

Primary Examiner—James Lowe
Assistant Examiner—Jeremiah F. Durkin II
Attorney, Agent, or Firm—Jordan B. Bierman

[57] ABSTRACT

A method of destroying a brittle body by molding around an elastic tube or an elastic tube in which is inserted a plastic wire or a heat-fusible member for defining a charging hole where the member or tube is partly exposed at the surface of the brittle body, and, after pulling out the elastic tube or fusing the heat-fusible member, an expandable splitting agent capable of expanding by hydration is charged into the charging hole and subjected to hydration-expansion to destroy the brittle body. In another form, a water-impermeable film enclosing an expandable splitting agent capable of expanding by hydration therein is previously buried in a brittle body in a relation partly exposed at the surface of the brittle body, and, after aperturing the exposed end of the water-impermeable film, the expandable splitting agent is subjected to hydration-expansion to destroy the brittle body.

30 Claims, 3 Drawing Sheets

METHOD OF DESTROYING A BRITTLE BODY BY HYDRATION EXPANSION

BACKGROUND OF THE INVENTION

This invention relates to a brittle body which is prepared to be destroyed later and relates also to a method of destroying the same. More particularly, this invention relates to a dental working cast which can be destroyed to take out a denture therefrom without damaging the denture and relates also to a method of destroying the same.

Denture is generally classified into a full denture and a partial denture. According to a prior art method of producing such dentures, an impression is first taken from the oral cavity of a patient, and slurry of gypsum is then poured into this impression to obtain a dental working cast. Then, a wax bite rim is formed on the working cast, and artificial teeth are arranged on the wax bite rim. The working cast having the artificial teeth arranged thereon is then placed in a flask, and, while pouring slurry of gypsum into the flask to embed the working cast in the block of gypsum, they are heated to fuse away the wax thereby obtaining a negative. A resin is then charged into the negative. Subsequently, the negative having the resin charged therein is heated to cure the resin, and the working cast containing the denture formed by the combination of the resin and the artificial teeth embedded in the working cast is deflasked. Thereafter, the denture is dug out of the working cast to separate it from the working cast. The gypsum used to form the working cast is ordinary gypsum, hard gypsum, super-hard gypsum or the like. For separating the denture from the working cast, a tool such as a plaster forceps is employed to destroy the working cast. Therefore, considerable skill is required, and, also, much labor and a large length of time are required for the removing of the denture. It is the fact that several dentures at the most can be separated in a day. Also, such a method has frequently given rise to breakdown or permanent deformation of a denture.

With a view to solve the above problem, the applicant has proposed a method of destroying such a brittle mold by the use of an expandable splitting agent capable of expanding by hydration, as filed in Japanese OPI Nos. 60-185546 and 60/193456 (1985). Application of this method to the working cast described above has successfully solved the prior art problem pointed out above.

However, in the method proposed already by the applicant, it is necessary to bore a hole in the working cast by a drilling machine such as a small-sized electric drill for charging the expansive splitting agent capable of expanding by hydration into the working cast. Therefore, the drilling operation must be carefully done so as not to impair or damage the artificial teeth embedded in the working cast, and, in addition, the method involves a problem of emvironmental pollution by shavings produced as a result of drilling. Also, there is a limit in the repeated use of the electric drill, and the durability of the electric drill has posed another problem.

SUMMARY OF THE INVENTION

In view of the present status of the art as described above, it is a primary object of the present invention to provide a brittle body which makes it unnecessary to bore a hole for charging the expansive splitting agent therein, thereby obviating various problems including the problem of environmental pollution, and also to provide a method of destroying the same.

In accordance with one aspect of the present invention, there is provided a brittle body comprising a charging-hole defining member defining a hole into which an expandable splitting agent capable of expanding by hydration is charged, the member being substantially buried in the brittle body except that it is partly exposed at the surface of the brittle body. The charging-hole defining member is preferably one of an elastic tube, an elastic tube in which is inserted a plastic wire, a heat-fusible member and an expandable splitting member formed by enclosing the expansive splitting agent capable of expanding by hydration in a water-impermeable film.

In accordance with another aspect of the present invention, there is provided a method of destroying a brittle body comprising the steps of previously burying an elastic tube or an elastic tube in which is inserted a plastic wire in the brittle body during molding the brittle body in such a relation that the elastic tube is partly exposed at the surface of the brittle body, withdrawing the elastic tube from the brittle body to define a charging hole, charging an expansive splitting agent capable of expanding by hydration into the charging hole, and causing hydration-expansion of the an expandable splitting agent in the hole thereby destroying the brittle body.

In accordance with still another aspect of the present invention, there is provided a method of destroying a brittle body comprising the steps of previously burying a heat-fusible member in the brittle body during molding the brittle body in such a relation that the heat-fusible member is partly exposed at the surface of the brittle body, fusing the heat-fusible member to define a charging hole, charging an expandable splitting agent capable of expanding by hydration into the charging hole, and causing hydration-expansion of the expandable splitting agent in the hole thereby destroying the brittle body. By heat-fusible Applicants refer to substances which, when heated, are capable of flowing and can therefore be removed from the opening in which they were placed.

In accordance with yet another aspect of the present invention, there is provided a method of destroying a brittle body comprising the steps of previously burying an expandable splitting member, formed by enclosing an expandable splitting agent capable of expanding by hydration in a water-impermeable film, in the brittle body during molding the brittle body in such a relation that the an expandable splitting member is partly exposed at the surface of the brittle body, aperturing the end of the an expandable splitting member exposed at the surface of the brittle body, and causing hydration-expansion of the an expandable splitting agent enclosed in the water-impermeable film thereby destroying the brittle body.

DESCRIPTION OF THE PREFERRED EMBODIMENTS

A first embodiment of the present invention will now be described in detail with reference to FIGS. 1 to 5, in which a dental working cast is (referred to hereinafter simply as a cast) used as one form of a brittle body for digging out a denture from the cast.

Figure 1:
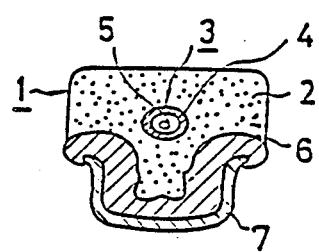
FIGS. 1 and 2 are a sectional front elevation view and a sectional side elevation view respectively to illustrate how a working cast for making a denture is produced from a tooth impression according to a first embodiment of the present invention.
Figure 2:
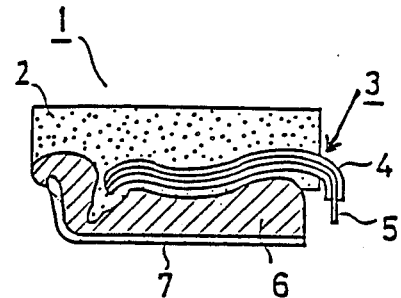
Figure 3:
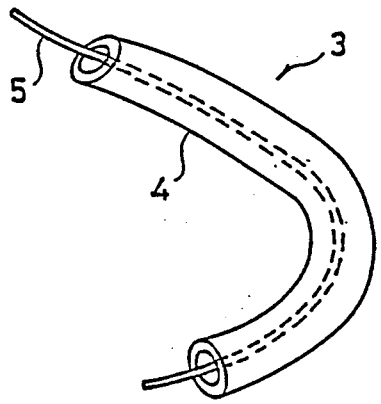
FIGS. 3, 4 and 5 are a perspective view, a sectional view and a perspective view respectively illustrating various forms of the charging-hole defining member shown in FIGS. 1 and 2.
Figure 4:
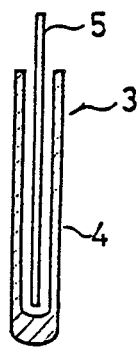
Figure 5:
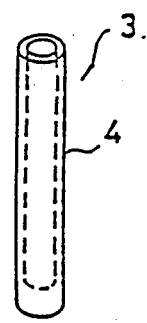

First, a tray 7 having an impression-providing material 6 packed therein is pressed against teeth in the oral cavity of a patient to take the impression of the teeth. The impression thus taken provides a negative of the impression of the teeth of the patient, as shown in FIGS. 1 and 2. Then, slurry of gypsum is poured into the negative formed by the impression-providing material 6 packed in the tray 7 to produce a cast 1 as shown in FIG. 1. During molding the cast 1, a charging-hole defining member 3 is buried in the block of gypsum according to the plan of later splitting of the cast 1, in such a relation that the charging-hole defining member 3 is partly exposed at the surface of the cast 1. The charging-hole defining member 3 employed in the first embodiment is such that a plastic member 5 is inserted in an elastic tube 4 as shown in FIG. 3. When a force is imparted to shape or bend the plastic or bendable member 5 into a desired form and the force is then removed, the plastic or bendable member 5 remains in the deformed shape. Therefore, the charging-hole defining member 3 can be easily buried in a horseshoe shape in the gypsum block along the negative formed by the impression-providing material 6. A tube of an elastic material such as rubber may be used as the elastic tube 4, and a wire of a plastic or bendable material such as soft iron, brass or copper may be used as the plastic or bendable member 5. The sectional shape of the elastic tube 4 may be any one of various shapes including a circular shape, an elliptical shape and a rhombic shape, taking into consideration the directions of splitting by an expandable splitting agent capable of expanding by hydration. In the illustrated embodiment, the charging-hole defining member 3 is buried in a horseshoe pattern and protrudes at its both ends from the cast 1. However, the mode of burying the charging-hole defining member 3 is in no way limited to that described above, and the charging-hole defining member 3 may protrude from the cast 1 at one end only and may be buried in the cast 1 at the other end. In such a case, the other end of the member 3 buried in the cast 1 is preferably closed as shown in FIG. 4. Also, when the member 3 is to be buried in a straight pattern, the plastic member 5 may be eliminated as shown in FIG. 5.

Upon lapse of several minutes after burying the charging-hole defining member 3 in the poured slurry of gypsum, the gypsum slurry cures to form a gypsum layer 2 thereby completing the cast 1. Then, when one of the protruding ends of the charging-hole defining member 3 is grasped by the hand and pulled, the elastic tube 4 is stretched, and its diameter is decreased, so that the elastic tube 4 can be very simply withdrawn from the cast 1. Subsequently, the steps including formation of a wax bite rim, arrangement of artificial teeth and thermal curing of a resin are carried out according to a known method. The denture is then dug out as described hereinafter.

First, a expandable splitting agent capable of expanding by hydration is charged into the charging hole defined or formed as a result of pull-out of the charging-hole defining member 3. The expandable splitting agent capable of expanding by hydration preferably employed in the present invention is a known one, for example, "BRISTAR" (trade name, made by Onoda Cement Co., Ltd.), "S-MITE" (made by Sumitomo Cement Co., Ltd.), "CALMMITE" (made by Nippon Cement Co., Ltd.) or "DENKA-CHEMI AXE" (made by DENKI KAGAKU KOGYO KABUSHIKI KAISHA),. Also, a so-called cement-concrete expanding agent may be employed, which is a material or a mixture selected from a group including, for example, lime, calcium sulfoaluminate, calcinated dolomite, magnesia, ordinary portland cement-blast furnace slag-bauxite-gypsum, alumina cement-lime-gypsum, and calcium aluminate-lime-gypsum. Further, one or more of materials including quick lime and baked dolomite may be employed, and a hydrating reaction suppressor such as sodium silicofluoride, citric acid or tartaric acid may be mixed with the expanding agent, as required. The expandable splitting agent to be charged may be mixed with water to be turned into a slurry form. Besides the slurry form described above, the expansive splitting agent may be powdery or granular. When the an expandable splitting agent is in the powdery or granular form, water is injected into the hole, or the cast 1 is bodily immersed in water.

In the cast where quick lime is used as the an expandable splitting agent, it is preferably supplied in a powdery or granular form, since quick lime is greatly consumed and tends to become crisp when supplied in a slurry form.

By merely leaving the an expandable splitting agent in the charged state, the gypsum layer 2 of the cast 1 can be split by the hydration expansion pressure caused by expansion of the splitting agent. However, the cast 1 is preferably placed in a high-temperature environment, for example, a steam bath, an air bath or a water bath having a temperature higher than about 20° C., so that the gypsum layer 2 can be destroyed within a very short period of time, and the denture can be easily removed from the cast 1.

A second embodiment of the present invention in which a heat-fusible member is employed as a charging-hole defining member for defining a hole for charging an expandable splitting agent as described above, will be described with reference to FIGS. 6 to 9.

Figure 6:
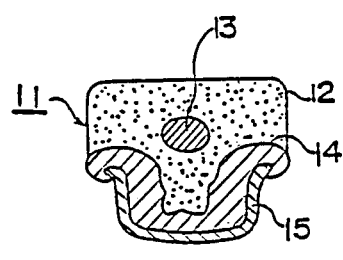
FIGS. 6 and 7 are a sectional front elevation view and a sectional side elevation view respectively to illustrate how a working cast for making a denture is produced from a tooth impression according to a second embodiment of the present invention.
Figure 7:
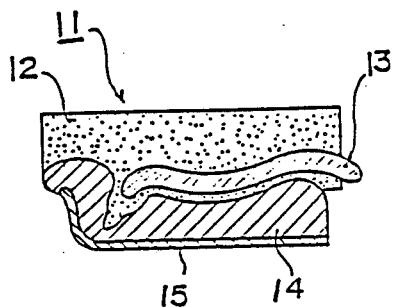
Figure 8:
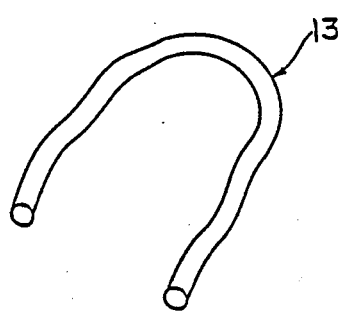
FIG. 8 is a perspective view of one form of the heat-fusible member shown in FIGS. 6 and 7.

First, a tray 15 having an impression-providing material 14 packed therein is pressed against teeth in the oral cavity of a patient to take the impression of the teeth. The impression thus taken provides a negative of the impression of the teeth of the patient, as shown in FIGS. 6 and 7. Then, slurry of gypsum is poured into the negative formed by the impression-providing material picked in the tray 15 to produce a cast 11 as shown in FIG. 6. During molding the cast 11, a heat-fusible member 13 is buried in the block of gypsum according to the plan of later destruction of the cast 11, in such a relation that the heat-fusible material 13 is partly exposed at the surface of the cast 11. The heat-fusible member 13 employed in this second embodiment is provided by shaping a solid wax into a horseshoe form as shown in FIG. 8. In the illustrated embodiment, the heat-fusible member 13 is buried in the horseshoe pattern and protrudes at its both ends from the cast 11. However, the mode of burying the heat-fusible member 13 is in no way limited to that described above, and the heat-fusible member 13 may protrude from the cast 11 at one end only and may be buried in the cast 11 at the other end. The sectional shape of the heat-fusible member 13 may be any one of various shapes including a circular shape, an elliptical shape, a rhombic shape and a T-like shape, taking into consideration the directions of splitting by an expandable splitting agent as described already.

The material of the heat-fusible member 13 preferably employed in the present invention is a waxy material such as animal fat, solid vegetable oil, solid wax, paraffin wax, polyethlene glycol, a polyethylene glycol ester, a polyethylene glycol ether, polypropylene glycol, a polypropyrene glycol ester, or a polypropyrene glycol ether; or a thermoplastic resin such as polyethylene, polystyrene, polyvinyl chloride, or polymethyl methacrylate. In the case of the thermoplastic resin, that having a low melting point and having a specific gravity lower than that of gypsum is preferably employed. In such a thermoplastic resin, a plasticizer, for example, a phathalic ester such as dibutyl phathalate or dioctyl phthalate; a phosphoric ester such as tributyl phosphate; glycol or glycerol such as polyethylene glycol or tributyl citrate, is preferably used. The heat-fusible member employed for destroying a dental working cast as described above is preferably such that it is fused simultaneously with fusion of the wax bite rim, that is, its melting point is lower than about 60° C.

In this second embodiment of the present invention, the heat-fusible member shaped into a rod form or a web form is buried in a brittle body to be destroyed. In this case, the heat-fusible member may be shaped into any form conforming to the plan of destroying the brittle body.

Figure 9:
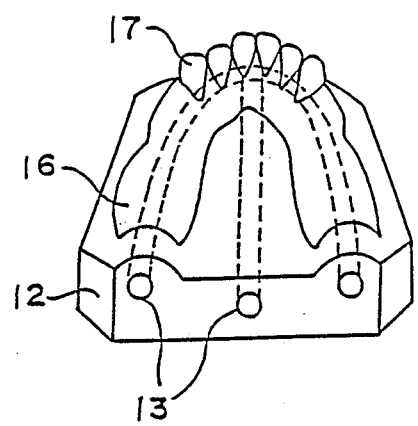
FIG. 9 is a perspective view showing one of the steps of producing the denture according to the second embodiment of the present invention.

FIG. 9 illustrates that a heat-fusible member 13 shaped into a horseshoe form is buried together with another heat-fusible member 13 shaped into a rod-like form.

Upon lapse of several minutes after burying such heat-fusible member 13 in the poured slurry of gypsum, the gypsum slurry cures to form a gypsum layer 12 thereby completing the cast 11. Subsequently, the steps including formation of a wax bite rim 16 and arrangement of artificial teeth 17 are carried out according to a known method. Then, the wax bite rim 16 is fused away to produce a negative as described already, and a resin poured into the negative is subjected to thermal curing. The heat-fusible members 13 are preferably fused simultaneously with the fusion of the wax bite rim 16.

The steps of digging out the denture from the cast 11 molded in the manner described above include fusing the heat-fusible members 13 to form charging cavities and charging the expansive splitting agent into the cavities.

The an expandable splitting agent preferably employed in the present invention is a known one, for example, "BRISTAR" (trade name, made by Onoda Cement Co., Ltd.), "S-MITE" (made by Sumitomo Cement Co., Ltd.), "CALMMITE" (made by Nippon Cement Co., Ltd), "DENKA-CHEMI AXE" (made by DENKI KAGAKU KOGYO KABUSHIKI KAISHA). The foregoing trademarks are used by the respective manufacturers on mixtures consisting primarily of $SiO_2$, $Al_2O_3$, $Fe_2O_3$, $CaO$, $MgO$, and $SO_3$. Also a so-called cement-concrete expanding agent may be employed, which is a material or a mixture selected from a group including, for example, lime, calcium sulfoaluminate, calcinated dolomite, magnesia, ordinary portland cement-blast furnace sslag-bauxite-gypsum, alumina cement-lime-gypsum, and calcium aluminate-lime-gypsum. Further, one or more of materials including quick lime and baked dolomite may be employed, and a hydrating reaction suppressor such as sodium silicofluoride, citric acid or tartaric acid may be mixed with the expanding agent, as required.

A third embodiment of the present invention will be described in detail with reference to FIGS. 10 to 13, in which an expandable splitting member formed by enclosing an expandable splitting agent as described above in a water-impermeable film is used as a charging-hole defining member defining a hole for charging the expandable splitting agent.

Figure 10:
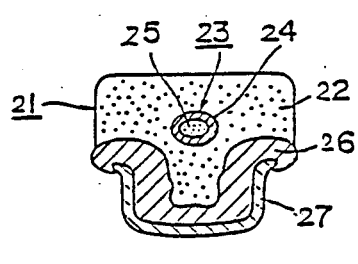
FIGS. 10 and 11 are a sectional front elevation view and a sectional side elevation view respectively to illustrate how a working cast for making a denture is produced from a tooth impression according to a third embodiment of the present invention.
Figure 11:
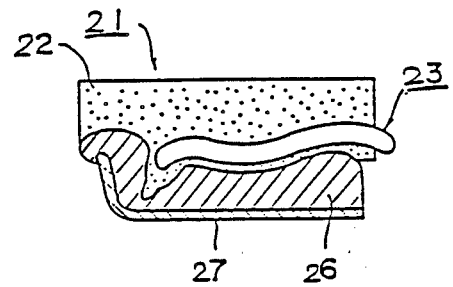
Figure 12:
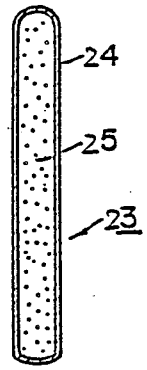
FIG. 12 is a longitudinal sectional view of one form of the expandable splitting member shown in FIGS. 10 and 11.

First, a tray 27 having an impression-providing material 26 packed therein is pressed against teeth in the oral cavity of a patient to take the impression of the teeth. The impression thus taken provides a negative of the impression of the teeth of the patient, as shown in FIGS. 10 and 11. Then, slurry of gypsum is poured into the negative formed by the impression-providing material 26 packed in the tray 27 to produce a cast 21 as shown in FIG. 10. During molding the cast 21, an expandable splitting member 23 is buried in the block of gypsum according to the plan of later destruction of the cast 21, in such a relation that the expandable splitting member 23 is partly exposed at the surface of the cast 21. The expandable splitting member 23 employed in this third embodiment is such that an expandable splitting agent capable of expanding by hydration 25 is enclosed in a water-impermeable film 24 as shown in FIG. 12. In the case of the illustrated embodiment, two expandable splitting members 23 are each buried to protrude at one end from the cast 21. One of such expandable splitting members 23 may be elongate and may be buried ina horseshoe pattern along the outer edge of the cast 21. Such an expandable splitting member 23 may protrude at one or both ends from the cast 21.

The an expandable splitting agent preferably employed in the present invention is a known one, for example, "BRISTAR" (trade name, made by Onoda Cement Co., Ltd.), "S-MITE" (made by Sumitomo Cement Co., Ltd.), "CALMMITE" (made by Nippon Cement Co., Ltd.) or "DENKA-CHEMI AXE" (made by DENKI KAGAKU KOGYO KABUSHIKI KAISHA). Also, a so-called cement-concrete expanding agent in a powdery or granular form may be employed, which is a material or a mixture selected from a group including, for example, lime, calcium sulfoaluminate, calcinated dolomite, magnesia, ordinary portland cement-blast furnace slag-bauxite-gypsum, alumina cement-lime-gypsum, and calcium aluminate-lime-gypsum. Further, one or more of materials including quick lime and baked dolomite may be employed, and a hydration reaction suppressor such as sodium silicofluoride, citric acid or tartaric acid may be mixed with the expanding agent of powdery or granular form, as required.

The material of the water-impermeable film preferably employed in the present invention is polyethylene, polyvinyl chloride, nylon, natural rubber, synthetic rubber, aluminum foil or any one of various laminates. The water-impermeable film has preferably a suitable expansibility or fragility to permit hydration-expansion of the expandable splitting agent enclosed therein. In the present invention, the expandable splitting agent is enclosed or sealed in such a water-impermeable film to provide the expandable splitting member. This expandable splitting member may be furnished in, for example, a rod form or a web form. Also, when the expandable splitting member is required to be buried in the brittle body after being bent into a desired shape, a plastic or bendable wire or web may be enclosed in or mounted on part of the outer wall of the water-impermeable film. Further, the expandable splitting member of, for example, rod form supported by a plastic or bendable wire may be buried in the brittle body after being bent into a desired shape. Furthermore, the expandable splitting agent may be filled in the water-impermeable film shaped into a desired form to provide the static expandable splitting member. Also, a plurality of such static expandable splitting members may be connected together, and one or more of the connected static expandable splitting members may be suitably separated by breaking the connections as required.

Figure 13:
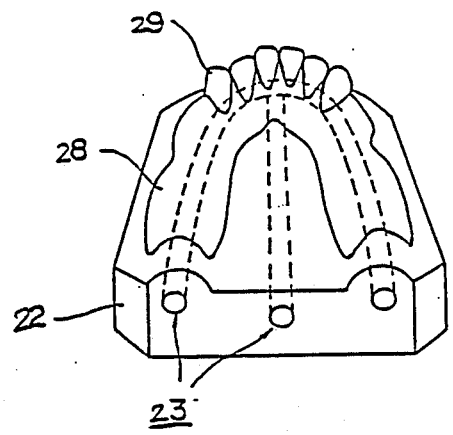
FIG. 13 is a perspective view showing one of the steps of producing the denture according to the third embodiment of the present invention.

FIG. 13 illustrates that an expandable splitting member 23 shaped into a horseshoe form is buried together with another expandable splitting member 23 shaped into a rod-like form.

Upon lapse of several minutes after buring such expandable splitting members 23 in the poured slurry of gypsum, the gypsum slurry cures to form a gypsum layer 22 thereby completing the cast 21. Subsequently, the steps including formation of a wax bite rim 28 and arrangement of artificial teeth 29 are carried out according to a known method. Then, the wax bite rim 28 is fused away to produce a negative as described already, and a resin poured into the negative is subjected to thermal curing. The water-impermeable films 24 of the expandable splitting members 23 are required that they may not be destroyed during the fusion of the wax bite rim 28 and the thermal curing of the resin.

The steps of digging out the denture from the cast 21 by destroying the cast 21 molded in the manner described already include aperturing the ends of the water-impermeable films 24 of the expandable splitting members 23 buried in the cast 21 and causing hydration-expansion of the expandable splitting agent 25 contained in the members 23. This hydration-expansion can be caused by pouring water through the apertures of the water-impermeable films 24 or immersing the cast 21 in water.

It will be understood from the foregoing detailed description of the present invention that a charging-hole defining member defining a hole for charging an static expandable splitting agent is previously buried in a brittle body, so that a drilling operation for boring such a hole is unnecessary, and the problem of environmental pollution due to shavings produced as a result of drilling can also be solved. Application of the present invention to digging-out of a denture from a dental working cast is advantageous in that static splitting and removing of gypsum can prevent permanent deformation and injury of the denture, so that the denture thus produced fits satisfactorily to the oral cavity of a specific patient. The aforementioned embodiments of the present invention have referred to a dental working cast as an example of the brittle body. However, it is apparent that the present invention finds a variety of application besides the specific example described above. For example, the present invention is applicable to destruction of a brittle body for the production of a gold crown or a metal-based denture or orthodontic appliance and also applicable to destruction of a brittle body of mortar, concrete or the like to be destroyed or scheduled to be destroyed.

What we claim is:

1. A method of destroying a brittle body comprising partially embedding a heat-fusible member in said body during molding thereof so that said member is partially exposed at the surface of said body, fusing said member to define a hole, introducing an expandable splitting agent capable of expanding by hydration into said hole in an unexpanded state, and causing hydration expansion of said agent thereby resulting in destruction of said body.

2. The method of claim 1 wherein said heat-fusible member is a material selected from the group consisting of animal fats, solid vegetable oils, solid waxes, polyethylene glycols, polyethylene glycol ethers, polyethylene glycol esters, polypropylene glycols, polypropylene glycol ethers, polypropylene glycol esters, polyethylene, polystyrene, polyvinyl chloride, and polymethyl methacrylate.

3. The method of claim 1 wherein said agent is in a powder or granular form and is introduced into said hole and water is then injected into said hole to cause hydration-expansion of said agent.

4. The method of claim 1 wherein said agent is charged in said hole, said body is then immersed in water to cause the hydration-expansion of said agent.

5. The method of claim 1 wherein said body having said agent therein is placed in a high-temperature atmosphere provided by a steam bath, an air bath or a water bath to promote the hydration-expansion of said agent.

6. The method of claim 1 wherein water is added to said agent to obtain slurry of said agent, and said slurry is then charged in said hole to cause the hydration-expansion of said agent.

7. The method of claim 1 wherein said agent is selected from the group consisting of cement-concrete expanding agent, quick lime, or baked dolomite.

8. The method of claim 1 wherein a hydration reaction suppressor is mixed with said agent.

9. The method of claim 8 wherein said suppressor is taken from the class consisting of sodium silicofluoride, citric acid, and tartaric acid.

10. The method of claim 1 wherein said body is a dental cast.

11. A method of destroying a brittle body comprising partially embedding an elastic tube in said body during the molding thereof, said elastic tube being embedded so that said tube is partially exposed at the surface of said body, withdrawing said tube from said body thus leaving a hole, introducing an expandable splitting agent capable of expanding by hydration into said hole in an unexpanded state, and causing hydration-expansion of said agent thereby resulting in the destruction of said body.

12. The method of claim 11 wherein there is a pliable member inside said tube, including the step of bending said tube and said member to conform to the shape of said body.

13. The method of claim 11 wherein said agent is selected from the group consisting of cement-concrete expanding agent, quick lime, or baked dolomite.

14. The method of claim 11 wherein a hydration reaction suppressor is mixed with said agent.

15. The method of claim 14 wherein said suppressor is taken from the class consisting of sodium silicofluoride, citric acid, and tartaric acid.

16. The method of claim 11 wherein said body having said agent therein is placed in a high-temperature atmosphere provided by a steam bath, an air bath or a water bath to promote the hydration-expansion of said agent.

17. The method of claim 11 wherein said agent is in a powder or granular form and is introduced into said hole and water is then injected into said hole to cause hydration-expansion of said agent.

18. The method of claim 17 wherein said agent is charged in said hole, and said brittle body is then immersed in water to cause the hydration-expansion of said agent.

19. The method of claim 11 wherein water is added to said agent to obtain slurry of said agent, and said slurry is then charged in said hole to cause hydration-expansion of said agent.

20. The method of claim 11 wherein said body is a dental cast.

21. A method of destroying a brittle body comprising partially embedding an expandable splitting member containing an expandable splitting agent capable of expanding by hydration in said body during molding thereof, said member being partially exposed at the surface of said body, forming an aperture in the exposed portion of said member, and causing hydration-expansion of said agent thereby resulting in the destruction of said body.

22. The method of claim 21 wherein said body having said agent therein is placed in a high-temperature atmosphere provided by a steam bath, an air bath or a water bath to promote the hydration-expansion of said agent.

23. The method of claim 21 wherein said body is immersed in water to cause hydration-expansion of said agent.

24. The method of claim 21 wherein said member comprises a water impermeable film taken from the class consisting of polyethylene, polyvinyl chloride, nylon, natural rubber, synthetic rubber, aluminum foil, and laminated film having a suitable expandability or fragility, thereby permitting expansion of said agent enclosed therein.

25. The method of claim 21 wherein water is injected through said aperture to cause hydration-expansion of said agent.

26. The method of claim 21 wherein said agent is selected from the group consisting of cement-concrete expanding agent, quick lime, or baked dolomite.

27. The method of claim 21 wherein a hydration reaction suppressor is mixed with said agent.

28. The method of claim 27 wherein said suppressor is taken from the class consisting of sodium silicofluoride, citric acid, and tartaric acid.

29. The method of claim 21 wherein said agent is in a powder or granular form and is introduced into said hole and water is then injected into said hole to cause hydration-expansion of said agent.

30. The method of claim 21 wherein said body is a dental cast.

* * * * *